(12) United States Patent
Goutsis et al.

(10) Patent No.: US 9,283,158 B2
(45) Date of Patent: Mar. 15, 2016

(54) OXIDANT PREPARATION HAVING OPTIMIZED VISCOSITY FOR TREATING KERATIN FIBERS

(71) Applicant: Henkel AG & Co. KGaA, Duesseldorf (DE)

(72) Inventors: Konstantin Goutsis, Juechen (DE); Juergen Schoepgens, Schwalmtal (DE); Marc Krippahl, Moenchengladbach (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/334,200

(22) Filed: Jul. 17, 2014

(65) Prior Publication Data

US 2014/0325768 A1    Nov. 6, 2014

Related U.S. Application Data

(63) Continuation of application No. PCT/EP2013/051541, filed on Jan. 28, 2013.

(30) Foreign Application Priority Data

Jan. 31, 2012   (DE) .................. 10 2012 201 338

(51) Int. Cl.
*A61Q 5/10* (2006.01)
*A61K 8/22* (2006.01)
*A61K 8/73* (2006.01)
*A61K 8/31* (2006.01)
*A61K 8/92* (2006.01)

(52) U.S. Cl.
CPC ... *A61K 8/22* (2013.01); *A61K 8/31* (2013.01); *A61K 8/73* (2013.01); *A61K 8/922* (2013.01); *A61Q 5/10* (2013.01); *A61K 2800/48* (2013.01)

(58) Field of Classification Search
CPC ............ A61Q 5/08; A61K 8/22; A61K 8/34; A61K 8/73
USPC ........................................... 424/62
See application file for complete search history.

(56) References Cited

U.S. PATENT DOCUMENTS

| | | | |
|---|---|---|---|
| 4,904,275 A | 2/1990 | Grollier | |
| 4,927,627 A | 5/1990 | Schrader et al. | |
| 6,641,618 B1 * | 11/2003 | Legrand et al. | .......... 8/101 |
| 8,425,623 B2 | 4/2013 | Goutsis et al. | |
| 2002/0139957 A1 | 10/2002 | Matsuo et al. | |
| 2003/0086882 A1 * | 5/2003 | Schmenger et al. | ........... 424/62 |
| 2010/0307527 A1 | 12/2010 | Bureiko et al. | |
| 2011/0067722 A1 | 3/2011 | Bureiko et al. | |

FOREIGN PATENT DOCUMENTS

| | | | | |
|---|---|---|---|---|
| DE | 102200403017 A1 * | 2/2006 | ............. | A61Q 5/08 |
| DE | 102010003264 A1 | 9/2011 | | |
| WO | 2010/062138 A2 | 6/2010 | | |

OTHER PUBLICATIONS

STIC Search Report dated Oct. 6, 2014.*
English translation of the Patent No. DE 102004030178 A1 dated Jan. 15, 2015.*
PCT International Search Report (PCT/EP2013/051541) dated Oct. 17, 2014.
Database GNPD [Online] Mintel, "Natural Bleach & Colour", XP002731269, Database Accession No. 849228, Jan. 2008.
Database GNPD [Online] Mintel, "Highlights Hair Colour", XP002731270, Database Accession No. 1666753, Nov. 2011.
Database GNPD [Online] Mintel, "Hydrating Gentle Facial Cleanser", XP002731271, Database Accession No. 10224698, Jul. 2005.
Database GNPD [Online] Mintel, "Natural Bleach Colour", XP002731272, Database Accession No. 1203289, Sep. 2009.
Database GNPD [Online] Mintel, "Medium Brown Hair Colorant", XP002731273, Database Accession No. 811029, Nov. 2007.
Schrader: "Grundlagen und Rezepturen der Kosmetika", (translation Basics and recipes of cosmetics), 2., verbesserte und erweiterte Auflage, 1989, Huthig Buch Verlag Heidelberg, pp. 1-20 (book table of contents), English abstract machine translation only.

* cited by examiner

*Primary Examiner* — Eisa Elhilo
(74) *Attorney, Agent, or Firm* — David K. Benson

(57) ABSTRACT

An oxidizing agent preparation for treating keratinic fibers, in particular human hair, includes in a cosmetic carrier (a) 0.01 to 25.0 wt. % of hydrogen peroxide, (b) 0.01 to 15.0 wt. % of one or more organic lipophilic compound(s) from the group of plant and animal fats, oils and waxes, paraffin hydrocarbons, $C_{10}$-$C_{24}$ fatty alcohols, silicone oils and dialkyl ethers of formula (I), in which R1 and R2 mutually independently denote an unbranched or branched $C_8$-$C_{24}$ alkyl group, and (c) 0.01 to 2.00 wt. % of one or more organic thickeners from the group of polysaccharides with the proviso that the oxidizing agent preparation does not include any synthetic polymers of the polyacrylic acid type.

R1—O—R2    (I).

12 Claims, No Drawings

OXIDANT PREPARATION HAVING OPTIMIZED VISCOSITY FOR TREATING KERATIN FIBERS

FIELD OF THE INVENTION

The present invention generally relates to oxidizing agent preparations for treating keratinic fibers, in particular human. The present invention also provides a method for mixing and applying ready-to-use formulations for color modification of keratinic fibers using the oxidizing agent preparations.

BACKGROUND OF THE INVENTION

Depending on the requirements placed on the coloring result, a person skilled in the art is aware of various coloring systems for providing color-modifying cosmetic agents, in particular for keratinic fibers, such as for example hair. "Oxidation coloring agents", as they are known, are used for permanent, high intensity coloring results with corresponding fastness characteristics. Such coloring agents conventionally include oxidation dye precursors, known as "developer components" and "coupler components" which, under the influence of oxidizing agents such as for example hydrogen peroxide, react with one another to form the actual dyes. Oxidation coloring agents are distinguished by excellent, long-lasting coloring results. In addition to coloring, many consumers very specifically also wish to achieve lightening or blonding of their own hair color. To this end, the natural or artificial dyes coloring the fibers are decolorized, usually oxidatively using appropriate oxidizing agents, such as for example hydrogen peroxide.

In order to achieve optimum coloring and lightening performance, oxidative coloring or lightening agents generally require an alkaline pH value in use, optimum results in particular being achieved at pH values between 8.5 and 10.5.

Hydrogen peroxide is used as standard as an oxidizing agent both in oxidative coloring and in lightening or blonding of keratinic fibers. Aqueous hydrogen peroxide solution are, however, unstable at the alkaline pH values required for use, such that conventional commercial oxidative coloring and blonding products generally consist of at least two components. The first component is an acidified oxidizing agent preparation including hydrogen peroxide which is mixed shortly before use with an alkalized second component which for example assumes the form of a cream. In the case of an oxidative coloring product, said second component additionally includes oxidation dye precursors of the developer and/or coupler type.

The components can be mixed with the assistance of various mixing devices. One mixing method which is well-established primarily among home users is to transfer the two components into an applicator bottle, mix them to form a homogeneous formulation for use by shaking the bottle and then apply them onto the keratin fibers via an orifice in the applicator bottle. In another mixing method which is often used by hairdressers, the two components are placed in a mixing dish from where, once they have been carefully stirred or mixed together, they are applied onto the hair with the assistance of a paintbrush or an applicette.

Both methods place specific requirements on the packaging and viscosity of the formulations used in each case, wherein both the viscosities of the individual components (oxidizing agent preparation and alkaline (cream) component) and the viscosity of the final mixture for use make a substantial contribution to achieving a uniform and intense coloring or lightening result.

If, in the case of mixing in a mixing dish, individual formulations with excessively different viscosities are mixed together, blending to form a homogeneous formulation for use can be achieved only with difficulty or only after extended stirring. The viscosities of the oxidizing agent preparation and alkaline (cream) component must therefore be precisely adjusted to one another. In particular if one or both of the formulations used have an excessively high viscosity and are thus much too viscous, complete intermixing by stirring with a paintbrush can only be achieved with difficulty.

Furthermore, it must be ensured that the oxidizing agent preparation can be optimally discharged from the container in which it was provided for use. Said container usually comprises a flexible bottle with a small orifice from which the oxidizing agent preparation can be discharged by squeezing the bottle. Oxidizing agent preparations with an excessively high viscosity can be discharged only slowly, incompletely and by applying elevated pressure to the bottle.

Low-viscosity formulations can be transferred more readily from the bottle into the mixing dish, but are disadvantageous during subsequent mixing with the usually creamy, relatively high viscosity second component.

The viscosities of formulations which are intended to satisfy all the above-stated requirements, must therefore reliably be in a defined range which permits only a slight range of variation towards higher or lower viscosities.

The viscosity of formulations can be adjusted by using polymeric thickeners. If the viscosity of formulations including oxidizing agents is to be controlled, the thickener used must additionally be stable towards oxidizing agents.

Homo- and copolymers of acrylic acid or of methacrylic acid have hitherto proven to be the thickener system of choice for oxidizing agent formulations including hydrogen peroxide. Acrylic acid polymers and corresponding derivatives have elevated stability towards hydrogen peroxide, provide reliable thickening precisely in an alkaline environment and are compatible with electrolytes, salts and polar solvents.

Uncrosslinked or crosslinked polyacrylic acid polymers are used, for example in DE 10 2010 003 263 A1 and in DE 37 32 147 A1, for thickening oxidizing agent preparations. The oxidizing agent preparations described in DE 10 2010 003 264 A1 are biphasic systems which likewise include polyacrylic acid polymers for adjusting viscosity. Due to their poor biodegradability, however, efforts are increasingly being made to reduce the quantity of acrylic acid polymers used in cosmetic products or to replace them completely by natural thickeners or swelling agents with an improved environmental profile. Natural swelling agents, however, have the disadvantage that, if used in an excessively large amount, they can easily form a film on the skin. Such residues are not desired by consumers. If, on the other hand, the usage concentration of the biological swelling agents is reduced to such an extent that no residues remain on the skin after use, there is a risk that the viscosity cannot reliably be adjusted to the desired value over an extended storage period or the formulations will remain too thin.

It is therefore desirable to provide oxidizing agent preparations which make it possible to dispense with synthetic polymers, in particular polyacrylic acids, as a formulation component. It should here be possible reliably to adjust the viscosity of these formulations in such a manner that optimum intermixability with an alkaline (cream) component is ensured. Furthermore, it should be possible to discharge the oxidizing agent preparation completely from the container in which it is provided.

After intermixing, the formulation for use should have a viscosity which permits convenient application of the formulation onto the keratin fibers, wherein it should be possible for the formulation for use to be effectively distributed and give rise to uniform color change while, however, not dripping down from the consumer's head. Furthermore, all the thickeners used for adjusting viscosity should be biodegradable and not remain in the form of residues on the consumer's skin after use.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

It has surprisingly been found in the course of the work leading to the present invention that it is possible to adjust the viscosity of oxidizing agent preparations including hydrogen peroxide reliably to the desired specification range if a specific fatty base (organic lipophilic compound) and small quantities of a biodegradable polymer are used for this purpose.

An oxidizing agent preparation for treating keratinic fibers, in particular human hair, includes in a cosmetic carrier (a) 0.01 to 25.0 wt. % of hydrogen peroxide; (b) 0.01 to 15.0 wt. % of one or more organic lipophilic compound(s) from the group of plant and animal fats, oils and waxes, paraffin hydrocarbons, $C_{10}$-$C_{24}$ fatty alcohols, silicone oils and dialkyl ethers of formula (I),

$$R1\text{-}O\text{-}R2 \qquad (I)$$

in which R1 and R2 mutually independently denote an unbranched or branched $C_8$-$C_{24}$ alkyl group; and (c) 0.01 to 2.00 wt. % of one or more organic thickeners from the group of polysaccharides, with the proviso that the oxidizing agent preparation does not include a polymer which is obtained by polymerization or copolymerization of acrylic acid, does not a polymer which is obtained by polymerization or copolymerization of methacrylic acid, does not include a polymer which is obtained by polymerization or copolymerization of acrylic acid esters, does not include a polymer which is obtained by polymerization or copolymerization of methacrylic acid esters.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention firstly provides an oxidizing agent preparation for treating keratinic fibers, in particular human hair, including in a cosmetic carrier
(a) 0.01 to 25.0 wt. % of hydrogen peroxide,
(b) 0.01 to 15.0 wt. % of one or more organic lipophilic compound(s) from the group of plant and animal fats, oils and waxes, paraffin hydrocarbons, $C_{10}$-$C_{24}$ fatty alcohols, silicone oils and dialkyl ethers of formula (I),

$$R1\text{-}O\text{-}R2 \qquad (I)$$

in which
R1 and R2 mutually independently denote an unbranched or branched $C_8$-$C_{24}$ alkyl group, and
(c) 0.01 to 2.0 wt. % of one or more organic thickeners from the group of polysaccharides, with the proviso that the oxidizing agent preparation
does not include a polymer which is obtained by polymerization or copolymerization of acrylic acid,
does not include a polymer which is obtained by polymerization or copolymerization of methacrylic acid,
does not include a polymer which is obtained by polymerization or copolymerization of acrylic acid esters,
does not include a polymer which is obtained by polymerization or copolymerization of methacrylic acid esters.

Keratin-containing fibers are in principle taken to mean all kinds of animal hair, for example wool, horsehair, angora hair, furs, feathers and products or textiles manufactured therefrom. Preferably, however, the keratinic fibers are human hair.

The phrase "treating keratin fibers" used according to the invention is taken to mean any cosmetic treatment of keratinic fibers. In particular, said phrase includes color modification of the fibers. Color modification of keratin fibers includes any kind of color modification of the fibers. In particular, color modifications falling within the terms tinting, lightening, blonding, bleaching, oxidative coloring, semipermanent coloring, permanent coloring and temporary coloring are included. Color modifications which provide a lighter coloring result than the initial color, such as for example blonding with coloring, are explicitly also included according to the invention.

The oxidizing agent preparations according to the invention include the components essential to the invention in a cosmetic carrier, preferably in a suitable aqueous, alcoholic or aqueous-alcoholic carrier. Carriers suitable for the purpose of hair coloring are for example creams, emulsions, gels or also surfactant-containing foaming solutions, such as for example shampoos, mousse aerosols, mousse formulations or other preparations which are suitable for use on the hair.

The oxidizing agent preparations according to the invention include as the first essential formulation component (a) 0.01 to 25.0 wt. % of hydrogen peroxide.

The hydrogen peroxide may here be used itself as an aqueous solution and/or in the form of one of the solid addition products thereof onto organic or inorganic compounds. The basis for calculating the quantity ranges of 0.01 to 25.0 wt. % is 100% hydrogen peroxide.

In a preferred embodiment, hydrogen peroxide itself is used as an aqueous solution. The concentration of a hydrogen peroxide solution in the agent according to the invention is determined on the one hand by statutory requirements and on the other hand by the desired effect; oxidizing agent preparations which are preferred according to the invention are characterized in that they include 1.0 to 23.0 wt. %, further preferably 2.5 to 21.0 wt. %, more preferably 4.0 to 20.0 wt. % and particularly preferably 5.0 to 18.0 wt. % of hydrogen peroxide (calculated as 100% $H_2O_2$).

It has proven advantageous for the oxidizing agent preparations according to the invention additionally to include at least one stabilizer or complexing agent to stabilize the hydrogen peroxide. More preferred stabilizers are phenacetin, alkali metal benzoates (sodium benzoate) and salicylic acid. Any prior art complexing agents may furthermore be used. Complexing agents which are preferred according to the invention are nitrogen-containing polycarboxylic acids, in particular EDTA and EDDS, and phosphonates, in particular 1-hydroxyethane-1,1-diphosphonate (HEDP) and/or ethylenediamine-tetramethylenephosphonate (EDTMP) and/or diethylenetriaminepentamethylene-phosphonate (DTPMP) or the sodium salts thereof.

The oxidizing agent preparations according to the invention include as the second essential formulation component (b) 0.01 to 15.0 wt. % of one or more organic lipophilic compound(s) from the group of plant and animal fats, oils and waxes, paraffin hydrocarbons, $C_{10}$-$C_{24}$ fatty alcohols, silicone oils and dialkyl ethers of formula (I),

$$R1\text{-}O\text{—}R2 \tag{I}$$

in which
R1 and R2 mutually independently denote an unbranched or branched $C_8$-$C_{24}$ alkyl group.

For the purposes of the present invention, "organic lipophilic compounds" were taken to mean any suitable organic, lipophilic compounds which, under standard conditions (22° C., normal pressure), are insoluble or only sparingly solution in water and are therefore present in the oxidizing agent preparation in emulsified or dispersed form.

Plant and animal fats and oils are taken to mean solid, semisolid or liquid products from plant matter or animal carcasses which substantially consist of triacylglycerols (fatty acid triglycerides) of higher fatty acids.

A fatty acid triglyceride is taken for the purposes of the present invention to mean triesters of the trihydric alcohol glycerol with three equivalents of fatty acid. Both structurally identical and different fatty acids may participate in the ester bonds within a triglyceride molecule.

According to the invention, fatty acids should be taken to mean saturated or unsaturated, unbranched or branched, unsubstituted or substituted $C_8$-$C_{24}$ carboxylic acids. Unsaturated fatty acids may be mono- or polyunsaturated. In an unsaturated fatty acid, the C—C double bond(s) thereof may have cis or trans configuration.

For the purposes of the present invention, plant or animal waxes are taken to mean products from plant matter or animal carcasses which substantially consist of the esters of long-chain fatty acids ($C_{24}$-$C_{36}$ fatty acids, also known as "wax" acids) with long-chain alcohols ($C_{15}$-$C_{36}$-fatty alcohols).

Within the group of organic lipophilic compounds (b), plant oils and fats are preferred. The viscosity of oxidizing agent preparations which are formulated on the basis of emulsified or dispersed plant oils and fats can already reproducibly be adjusted to the desired range of values by using particularly small quantities of a biodegradable polysaccharide.

In a preferred embodiment of the present invention, the oxidizing agent preparation therefore includes a plant fat and/or a plant oil as the organic lipophilic compound (b).

The fatty acid triglycerides or triglyceride mixtures which occur in soy oil, peanut oil, olive oil, sunflower oil, macadamia nut oil, moringa oil, apricot kernel oil, marula oil, coconut oil and/or optionally hardened castor oil have proven particularly suitable for use as the fatty substance (organic lipophilic compound) in the oxidizing agent preparations according to the invention. Soy oil includes a mixture of triglycerides which is composed of the components palmitic acid, stearic acid, oleic acid, linoleic acid and linolenic acid. Peanut oil is mainly composed of the components palmitic acid, stearic acid, behenic acid, lignoceric acid, oleic acid and linoleic acid which are present in a form esterified with glycerol. Olive oil mainly consists of the fatty acid triglycerides made up of the components myristic acid, palmitic acid, oleic acid and linoleic acid. Sunflower oil mainly includes trifatty acid glycerides based on palmitic acid, stearic acid, oleic acid and linoleic acid. In the trifatty acid glycerides of macadamia nut oil, it is mainly the fatty acids linoleic acid, palmitic acid, arachidic acid and stearic acid which form the ester bonds with glycerol. Moringa oil includes a mixture of fatty acid triglycerides which is obtained by esterification of glycerol with the fatty acids myristic acid, palmitic acid, stearic acid, behenic acid, oleic acid and linoleic acid. The main components of apricot kernel oil are triglycerides with the fatty acids oleic acid and linoleic acid. The triglycerides of coconut oil are mainly composed of the fatty acids dodecanoic acid, tetradecanoic acid, oleic acid, palmitic acid, decanoic acid and octanoic acid and stearic acid. Marula oil substantially includes fatty acid triglycerides of glycerol and palmitic acid, stearic acid, oleic acid and linoleic acid.

From the above-stated group, it has in particular been found to be particularly advantageous to use a mixture of fatty acid triglycerides, as occurs in coconut oil, for adjusting the desired viscosity of the oxidizing agent preparations according to the invention.

Paraffin hydrocarbons may also be used as the organic lipophilic compound(s) (b). Paraffin hydrocarbons are a solid or liquid mixture of saturated, aliphatic hydrocarbons. This definition encompasses high viscosity liquid paraffin (Paraffinum liquidum), lower viscosity light liquid paraffin (Paraffinum perliquidum) and hard paraffin (Paraffinum solidum). Paraffin hydrocarbons are also known as paraffins, paraffin oils or paraffin waxes.

Oxidizing agent preparations which include paraffin hydrocarbons may be particularly effectively thickened with just small quantities of polysaccharides without any undesired or unpredictable effects occurring or the viscosity of the formulation varying over the course of time. It is therefore particularly preferable to use paraffin hydrocarbons as the organic lipophilic compound (b).

In a more preferred embodiment of the present invention, the oxidizing agent preparation therefore includes paraffin hydrocarbons as the organic lipophilic compound (b).

It is furthermore more preferable for the oxidizing agent preparation to include at least one plant fat, at least one plant oil and/or paraffin hydrocarbons as the organic lipophilic compound(s) (b).

It is furthermore likewise more preferable for the oxidizing agent preparation to include at least one plant fat and/or one plant oil and paraffin hydrocarbons as the organic lipophilic compound(s) (b).

$C_{10}$-$C_{24}$ fatty alcohols may also be used as the organic lipophilic compound(s) (b).

Unbranched or branched, saturated, mono- or polyunsaturated, aliphatic alcohols with 10 to 24 C atoms are designated as $C_{10}$-$C_{24}$ fatty alcohols. Examples of saturated $C_{15}$-$C_{24}$ fatty alcohols are decan-1-ol, undecan-1-ol, dodecan-1-ol (dodecyl alcohol, lauryl alcohol), tridecan-1-ol, tetradecan-1-ol (tetradecyl alcohol, myristyl alcohol), pentadecan-1-ol, hexadecan-1-ol (hexadecyl alcohol, cetyl alcohol, palmityl alcohol), heptadecan-1-ol, octadecan-1-ol (stearyl alcohol), nonadecan-1-ol, eicosan-1-ol (eicosyl alcohol, arachyl alcohol), heneicosan-1-ol and docosan-1-ol (docosyl alcohol, behenyl alcohol).

Examples of mono- or polyunsaturated $C_{10}$-$C_{24}$ fatty alcohols are (9Z)-octadec-9-en-1-ol (oleyl alcohol), (9E)-octadec-9-en-1-ol (elaidyl alcohol), (9Z,12Z)-octadeca-9,12-dien-1-ol (linoleyl alcohol), (9Z,12Z,15Z)-octadeca-9,12,15-trien-1-ol (linolenyl alcohol), (9Z)-eicos-9-en-1-ol (gadoleyl alcohol) and (5Z,8Z,11Z,14Z)-eicosan-5,8,11,14-tetraen-1-ol (arachidonic alcohol). Silicone oils may furthermore be used as the organic lipophilic compound(s) (b) in the oxidizing agent preparations according to the invention. The group of silicone oils above all encompasses linear, polymeric polydimethylsiloxanes which are synthesized according to the pattern $(R_2SiO)_x$ (with R=methyl) and have molar masses of between 1000 and 150000 g/mol. These oils are generally hydrophobic liquids.

Finally, dialkyl ethers of formula (I) may also be used as the organic lipophilic compound(s) (b), $$R1-O-R2 \quad (I)$$

in which
R1 and R2 mutually independently denote an unbranched or branched $C_8$-$C_{24}$ alkyl group.

The dialkyl ethers of formula (I) may be asymmetric, but are preferably symmetrically substituted.

Unbranched dialkyl ethers of formula (I) which may be mentioned by way of example are di-n-octyl ether, commercially available under the name Cetiol OE (INCI name: DICAPRYLYL ETHER) and di-n-stearyl ether. One example of dialkyl ethers of formula (I) with branched $C_8$-$C_{24}$ alkyl groups is di-2-ethylhexyl ether.

The organic lipophilic compound(s) (b) may be present in the oxidizing agent preparation according to the invention in a quantity of 0.01 to 15.0 wt. %. The weight range from 0.01 to 15 wt. % here relates to the sum all the lipophilic compounds (b) present in the oxidizing agent preparation. The organic lipophilic compounds (b) are preferably present in the oxidizing agent preparation in a quantity of 0.5 to 14.5 wt. %, further preferably of 5.0 to 14.0 wt. % and particularly preferably of 8.0 to 13.5 wt. %.

Another particularly preferred embodiment of the present invention is an oxidizing agent preparation which is characterized in that it includes as the organic lipophilic compound (b) 0.01 to 15.0 wt. %, preferably 0.5 to 14.5 wt. %, more preferably 5.0 to 14.0 wt. % and particularly preferably 8.0 to 13.5 wt. % of at least one plant fat, at least one plant oil and/or paraffin hydrocarbons.

The oxidizing agent preparations include as the third essential formulation component (c) 0.01 to 2.0 wt. % of one or more organic thickeners from the group of polysaccharides.

Organic thickeners from the group of polysaccharides (c) which may be used are representatives of celluloses (cellulose itself and the derivatives thereof), alginic acid (and the corresponding physiologically acceptable salts thereof, the alginates), agar-agar (with the polysaccharide agarose present as the main component in agar-agar), starch fractions and derivatives such as amylose, amylopectin and dextrins, karaya gum, locust bean flour, gum arabic, dextrans, guar gum and xanthan gum.

Suitable cellulose derivatives are methylcelluloses, ethylcelluloses, hydroxyalkylcelluloses (such as for example hydroxyethylcellulose), methylhydroxyalkylcelluloses and carboxymethylcellulose and the physiologically acceptable salts thereof.

Methylcelluloses are distributed for example under the name Culminal by Hercules or under the name Methocel by Dow. Hydroxypropylmethylcelluloses are for example commercially obtainable from Konimpex under the trade names Methylcellulose MK 70 M and Methylcellulose MK 10 M.

Physiologically acceptable salts of alginic acid which may for example be used are sodium alginate, ammonium alginate, calcium alginate and magnesium alginate.

Anionic polysaccharides are preferably selected from the group of polysaccharides (c) for thickening the oxidizing agent preparations according to the invention.

Carboxymethylcelluloses, alginic acids, xanthan gum and/or the physiologically acceptable salts thereof have proven particularly advantageous as anionic polysaccharides with regard to reliable viscosity adjustment and residue-free use on keratin fibers and the scalp.

In a further more preferred embodiment, the oxidizing agent preparations according to the invention include as the polysaccharide (c) at least one anionic polysaccharide which is selected from the group of carboxymethylcelluloses, alginic acids, xanthan gum and/or the physiologically acceptable salts thereof.

Carboxymethylcelluloses, alginic acids and xanthan gum, together with the physiologically acceptable salts thereof are likewise denoted for the purposes of the present invention as anionic polysaccharides, since the carboxylic acid groups present in these polysaccharides inevitably dissociate to a greater or lesser extent in water or a hydrous formulation, whereby anionic carboxylate groups are formed which further increase in number as the pH value rises. Since the oxidation coloring agent is used at alkaline pH values, the above-stated polysaccharides are therefore inevitably anionic when formulated. The polysaccharides (c) are present in the oxidizing agent preparation in quantities of 0.01 to 2.0 wt. %, preferably of 0.05 to 1.5 wt. %, further preferably of 0.1 to 1.0 wt. % and particularly preferably of 0.15 to 0.5 wt. %. The basis for calculating the stated quantity ranges is the sum of all the polysaccharides (c) present in the oxidizing agent preparation.

In a further preferred embodiment of the present invention, the oxidizing agent preparation is characterized in that it includes as the polysaccharide (c) 0.01 to 2.0 wt. %, preferably 0.05 to 1.5 wt. %, more preferably 0.1 to 1.0 wt. % and particularly preferably 0.15 to 0.5 wt. % of at least one anionic polysaccharide from the group of carboxymethylcelluloses, alginic acids, xanthan gum and/or the physiologically acceptable salts thereof.

In an explicitly more preferred embodiment of the present invention, the oxidizing agent preparation is characterized in that it includes as the anionic polysaccharide 0.01 to 2.0 wt. %, preferably 0.05 to 1.5 wt. %, further preferably 0.1 to 1.0 wt. % and particularly preferably 0.15 to 0.5 wt % of xanthan gum.

Xanthan gum is for example distributed under the trade name Keltrol by CP Kelco and under the name Rhodicare, Rhodopol and Rhodigel by Rhodia.

In a more preferred embodiment, the oxidation agent preparation is characterized in that it includes
(a) hydrogen peroxide
(b) liquid paraffin and
(c) xanthan gum in the quantity ranges as are disclosed in the priority-determining document in the table on pages 10-19.

The oxidizing agent preparations according to the invention may additionally include at least one organic solvent which is selected from 2-butoxyethanol, propylene glycol, propylene glycol monomethyl ether, diethylene glycol monomethyl ether, diethylene glycol monoethyl ether, ethylene glycol monobutyl ether, ethylene glycol monoethyl ether, ethanol, isopropanol, n-propanol, n-butanol, 1,2-propanediol, 1,3-propanediol, glycerol, 1-methoxy-2-propanol, 1-ethoxy-2-propanediol, 1,4-butanediol, 1,2-hexanediol, benzyl alcohol, phenoxyethanol, 2-phenylethyl alcohol, ethylene diglycol, methoxybutanol and n-butylene glycol. It is more preferable for the oxidizing agent preparation according to the invention additionally to include an organic solvent which is selected from propylene glycol and/or glycerol.

The solvents may be present in the oxidizing agent preparation in a quantity of 0.1 to 10.0 wt. %, preferably of 1.0 to 8.0 wt. %, further preferably of 2.0 to 7.0 wt. % and particularly preferably of 3.0 to 6.0 wt. %. The stated quantity ranges here relate to the sum of all the solvents from the above-stated groups present in the oxidizing agent formulation.

In a further more preferred embodiment, the oxidizing agent preparation according to the invention is characterized in that it additionally includes 0.1 to 10.0 wt. % of at least one organic solvent selected from 2-butoxyethanol, propylene glycol, propylene glycol monomethyl ether, diethylene glycol monomethyl ether, diethylene glycol monoethyl ether, ethylene glycol monobutyl ether, ethylene glycol monoethyl ether, ethanol, isopropanol, n-propanol, n-butanol, 1,2-propanediol, 1,3-propanediol, glycerol, 1-methoxy-2-propanol, 1-ethoxy-2-propanediol, 1,4-butanediol, 1,2-hexanediol, benzyl alcohol, phenoxyethanol, 2-phenylethyl alcohol, ethylene diglycol, methoxybutanol and n-butylene glycol, more preferably propylene glycol and/or glycerol.

In order to achieve the object of the invention, it has moreover proven advantageous for the oxidizing agent preparations additionally to include at least one organic carbonate. The diesters of carbonic acid, the carbonic acid being esterified with two organic residues, are designated as organic carbonates. The carbonic acid may here be esterified with two identical organic residues or with different organic residues. Cyclic carbonates have also proven very highly suitable in this connection. Cyclic carbonates are preferably substituted derivatives of the 1,3-dioxolan-2-one.

In a further more preferred embodiment the oxidizing agent preparation according to the invention is therefore characterized in that it additionally includes at least one organic carbonate of formula (II) and/or of formula (III), $$R3-O-\overset{\overset{O}{\|}}{C}-O-R4 \quad (II)$$

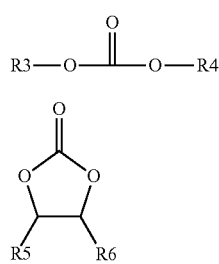

(III)

in which
R3, R4 mutually independently denote an unbranched $C_1$-$C_{30}$ alkyl group, a branched $C_3$-$C_{30}$ alkyl group or a mono- or polyunsaturated $C_2$-$C_{30}$ alkyl group,
R5, R6 mutually independently denote hydrogen, an unbranched $C_1$-$C_{30}$ alkyl group, a branched $C_3$-$C_{30}$ alkyl group, a mono- or polyunsaturated $C_2$-$C_{30}$ alkyl group or a hydroxy-$C_1$-$C_6$-alkyl group.

It is preferable for the residues R3 and R4 mutually independently to denote a methyl group, an ethyl group, an n-hexyl group, an n-octyl group or an n-decyl group or an n-dodecyl group.

It is furthermore preferable for the residues R3 and R4 of formula (II) to denote identical residues.

The residues R5 and R6 of formula (III) preferably mutually independently denote hydrogen, a methyl group, an ethyl group or a hydroxymethyl group.

It is more preferable for the oxidizing agent preparation additionally to include an organic carbonate of formula (II).

It is moreover likewise more preferable for the oxidizing agent preparation additionally to include an organic carbonate of formula (II) and an organic carbonate of formula (III). The organic carbonates of formula (II) and/or of formula (III) are present in the oxidizing agent preparation in quantities of 0.1 to 10.0 wt. %, preferably of 1.0 to 8.0 wt. %, further preferably of 2.0 to 7.0 wt. % and particularly preferably of 3.0 to 6.0 wt. %. The stated quantity ranges here relate to the sum of all the organic carbonates of formulae (II) and (III) present in the oxidizing agent preparation.

It has been found that it is possible to formulate particularly finely emulsified or dispersed emulsions with viscosity values which are stable over a long period of storage if the oxidizing agent preparations additionally include at least one organic carbonate which is selected from glycerol carbonate, propylene carbonate, ethylene carbonate, dimethyl carbonate, diethyl carbonate, di-n-hexyl carbonate, di-n-octyl carbonate, di-n-decyl carbonate and di-n-dodecyl carbonate.

It has above all proven advantageous in this connection to incorporate a compound from the group di-n-hexyl carbonate, di-n-octyl carbonate, di-n-decyl carbonate and di-n-dodecyl carbonate, particularly preferably di-n-octyl carbonate, into the oxidizing agent preparation as an additional component.

In a further more preferred embodiment, the oxidizing agent preparation according to the invention is characterized in that it additionally includes 0.1 to 10.0 wt. % of at least one organic carbonate selected from glycerol carbonate, propylene carbonate, ethylene carbonate, dimethyl carbonate, diethyl carbonate, di-n-hexyl carbonate, di-n-octyl carbonate, di-n-decyl carbonate and di-n-dodecyl carbonate, preferably di-n-octyl carbonate.

The ready-to-use oxidizing agent preparations are preferably provided as liquid preparations and at least one surface-active substance is additionally added to the agents, wherein depending on the field of use, such surface-active substances are designated surfactants or emulsifiers. They may in principle be selected from anionic, cationic, zwitterionic, amphoteric and nonionic surfactants and emulsifiers.

It has, however, been found in the course of the work leading to the present invention that the rheological properties of the oxidizing agent preparation are in particular advantageously influenced if the agents according to the invention include nonionogenic interfacially active substances. It is accordingly more preferable for the oxidizing agent preparation according to the invention additionally to include at least one nonionic surfactant.

Particularly suitable nonionic surfactants have here proven to be alkylene oxide addition products onto fatty alcohols with in each case 2 to 80 mol of ethylene oxide per mol of fatty alcohol.

A further particularly preferred embodiment of the present invention is characterized in that the oxidizing agent preparation additionally includes 0.1 to 10 wt. % of at least one polyethoxylated fatty alcohol of formula (IV),

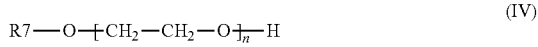

(IV)

in which
R7 denotes an unbranched or branched, saturated or unsaturated $C_{10}$-$C_{24}$ alkyl group and n denotes an integer from 2 to 80. R7 preferably denotes an unbranched, saturated $C_{12}$-$C_{18}$ alkyl group or an unbranched, monounsaturated $C_{12}$-$C_{18}$ alkyl group.

n preferably denotes an integer from 10 to 40, n particularly preferably denotes an integer from 10 to 25.

Examples of alkoxylated fatty alcohols of formula (IV) are Laureth-2, Laureth-3, Laureth-5, Laureth-8, Laureth-10 Laureth-12, Laureth-15, Laureth-20, Laureth-25, Laureth-30, Laureth-40, Laureth-50, Myreth-2, Myreth-3, Myreth-5, Myreth-8, Myreth-10, Myreth-12, Myreth-15, Myreth-20, Myreth-25, Myreth-30, Myreth-40, Myreth-50, Ceteth-2, Ceteth-3, Ceteth-5, Ceteth-8, Ceteth-10, Ceteth-12, Ceteth-15, Ceteth-20, Ceteth-25, Ceteth-30, Ceteth-40, Ceteth-50, Steareth-2, Steareth-3, Steareth-5, Steareth-8, Steareth-10, Steareth-12, Steareth-15, Steareth-20, Steareth-25, Steareth-30, Steareth-40, Steareth-50, Ceteareth-2, Ceteareth-3, Ceteareth-5, Ceteareth-8, Ceteareth-10, Ceteareth-12, Ceteareth-15, Ceteareth-20, Ceteareth-25, Ceteareth-30, Ceteareth-40, Ceteareth-50, Oleth-2, Oleth-3, Oleth-5, Oleth-8, Oleth-10, Oleth-12, Oleth-15, Oleth-20, Oleth-25, Oleth-30, Oleth-40 and Oleth-50. More preferably, Ceteth-12, Ceteth-20, Steareth-12, Steareth-20, Ceteareth-12, Ceteareth-20 and/or mixtures thereof are used as a nonionic surfactant in the oxidizing agent preparations according to the invention.

The polyethoxylated fatty alcohols of formula (IV) may be used in the oxidizing agent preparation in quantities of 0.1 to 10.0 wt. %, preferably of 0.5 to 7.5 wt. %, further preferably of 1.0 to 5.0 wt. % and particularly preferably of 1.5 to 2.5 wt. %. The stated quantity ranges here relate to the sum of all the compounds of formula (IV) present in the oxidizing agent preparation.

The agents according to the invention may furthermore also include nonionic surfactants of a type other than the polyethoxylated fatty alcohols together with anionic, cationic, zwitterionic and amphoteric surfactants. Nonionic surfactants which are likewise suitable have proven to be alkyl polyglycosides together with alkylene oxide addition products onto fatty acids with in each case 2 to 30 mol of ethylene oxide per mol of fatty alcohol or fatty acid. Preparations having excellent properties are likewise obtained if they include fatty acid esters of ethoxylated glycerol as the nonionic surfactants.

Further agents which are suitable according to the invention are characterized in that they additionally include at least one anionic surfactant. Preferred anionic surfactants are fatty acids, alkyl sulfates, alkyl ether sulfates and ether carboxylic acids with 10 to 20 C atoms in the alkyl group and up to 16 glycol ether groups per molecule. The anionic surfactants are used in proportions of 0.1 to 45 wt. %, preferably of 1 to 30 wt. % and particularly preferably of 1 to 15 wt. %, relative to the total quantity of the ready-to-use agent.

Agents according to the invention are characterized in that the agent additionally includes at least one zwitterionic surfactant. Particularly suitable zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. One preferred zwitterionic surfactant is known by the INCI name Cocamidopropyl Betaine.

The agents according to the invention may furthermore be characterized in that they additionally include at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. More preferred amphoteric surfactants are N-cocoalkyl aminopropionate, cocoacylaminoethyl aminopropionate and $C_{12}$-$C_{18}$ acylsarcosine.

The surfactants other than the polyethoxylated fatty alcohols of formula (IV) are used in proportions of 0.1 to 45 wt. %, preferably 1 to 30 wt. % and particularly preferably of 1 to 15 wt. %.

Agents which are suitable according to the invention may also include cationic surfactants of the quaternary ammonium compound, ester quat and amidoamine type. Preferred quaternary ammonium compounds are ammonium halides, and the imidazolium compounds known under the INCI names Quaternium-27 and Quaternium-83. Quaternized protein hydrolysates are further cationic surfactants which are usable according to the invention. One compound from the amidoamines which is particularly suitable according to the invention is stearamidopropyldimethylamine which is commercially available under the name Tegoamid® S 18. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. The agents used according to the invention preferably include the cationic surfactants in proportions of 0.05 to 10 wt. %, relative to the total agent.

In order to achieve an enhanced lightening and bleaching action, the oxidizing agent preparation may furthermore include at least one peroxo salt. Suitable peroxo salts are inorganic peroxo compounds, preferably selected from the group formed by ammonium peroxodisulfate, alkali metal peroxodisulfates, ammonium peroxomonosulfate, alkali metal peroxomonosulfates, alkali metal peroxodiphosphates and alkaline earth metal peroxides. Peroxodisulfates, in particular ammonium peroxodisulfate, potassium peroxodisulfate and sodium peroxodisulfate, are more preferred.

The persulfates are in each case present in the agent according to the invention in a quantity of 0.5 to 20 wt. %, preferably 1 to 12.5 wt. %, more preferably 2.5 to 10 wt. % and in particular 3 to 6 wt. %.

The oxidizing agent preparations may furthermore include additional active substances, auxiliary substances and additives in order to improve lightening performance and adjust further desired properties of the agents. It may accordingly prove advantageous for the agent to include at least one biologically safe thickener which differs from the agents of the first subject matter of the invention. Inorganic thickeners, in particular phyllosilicates such as for example bentonite, in particular smectites, such as montmorillonite or hectorite are suitable for this purpose.

The oxidizing agent preparation according to the invention is conventionally adjusted to an acidic pH value in order to stabilize the hydrogen peroxide contained therein. Acids which may be used are mineral acids (such as for example hydrochloric acid, sulfuric acid or phosphoric acid) or edible acids (such as for example citric acid, tartaric acid or malic acid). The desired pH value may also be adjusted by further organic acids from the group of phosphonic acid and/or diphosphonic acid, such as for example etidronic acid (1-hydroxyethane-1,1-diphosphonic acid), or from the group of heterocyclic acids, such as for example 2,6-dipicolinic acid (2,6-dicarboxypyridine).

The products used by a consumer or hairdresser for coloring or lightening/bleaching keratin fibers consist of at least two components packaged separately from one another. The oxidizing agent preparation according to the invention is here the first component which is mixed shortly before use with an alkalized second component. Said second component usually assumes the form of a cosmetic cream formulation and, in the case of an oxidative coloring product, also includes oxidation dye precursors and optionally additionally substantive dyes.

If the product is used as an oxidative coloring agent, the alkalized second component includes at least one oxidation dye precursor of the developer type and at least one oxidation dye precursor of the coupler type. Particularly suitable oxidation dye precursors of the developer type are here selected from at least one compound from the group which is formed by p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)-methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, 2,3- diamino-6,7-dihydro-1H,5H-pyrazolo[1,2-a]pyrazol-1-one and the physiologically acceptable salts thereof.

Particularly suitable oxidation dye precursors of the coupler type are here selected from the group formed by 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy) ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-meth-oxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts thereof.

In addition to oxidation dye precursors, the alkalized second component may also include substantive dyes. Substantive dyes may be subdivided into anionic, cationic and nonionic substantive dyes. The substantive dyes are preferably selected from nitrophenylenediamines, nitroaminophenols, azo dyes, anthraquinones, triarylmethane dyes or indophenols and the physiologically acceptable salts thereof. The additional substantive dyes are used in each case preferably in a proportion of 0.001 to 2 wt. %, relative to the entire preparation for use.

Preferred anionic substantive dyes are the compounds known by the international names or trade names Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1, Acid Black 52, bromophenol blue and tetrabromophenol blue.

Preferred cationic substantive dyes are cationic triphenylmethane dyes, such as for example Basic Blue 7, Basic Blue 26, Basic Violet 2 and Basic Violet 14, aromatic systems which are substituted with a quaternary nitrogen group, such as for example Basic Yellow 57, Basic Red 76, Basic Blue 99, Basic Brown 16 and Basic Brown 17, and substantive dyes which include a heterocycle which comprises at least one quaternary nitrogen atom, in particular Basic Yellow 87, Basic Orange 31 and Basic Red 51. The cationic substantive dyes distributed under the trademark Arianor are likewise cationic substantive dyes which are preferred according to the invention.

Suitable nonionic substantive dyes are in particular nonionic nitro and quinone dyes and neutral azo dyes. Preferred nonionic substantive dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 7, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]benzoic acid, 4-[(3-hydroxypropyl)amino]-3-nitrophenol, 4-nitro-o-phenylenediamine 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

The developer components, coupler components and optionally substantive dyes are preferably used in each case in a quantity of 0.0001 to 5.0 wt. %, preferably 0.001 to 2.5 wt. %, in each case relative to the ready-to-use agent. Developer components and coupler components are generally used in approximately molar quantities relative to one another. While molar use has also proven convenient, a certain excess of individual oxidation dye precursors is not disadvantageous, such that developer components and coupler components may be present in a molar ratio of 1:0.5 to 1:3, in particular 1:1 to 1:2.

Lightening and coloring processes on keratin fibers conventionally proceed in an alkaline environment. Establishing an excessively high pH value is, however, not desirable if the keratin fibers and also the skin are to be treated as gently as possible. The pH value of the ready-to-use agent may therefore be between 3 and 11. It is however preferred for the pH value of the ready-to-use agent to be between 7 and 11, in particular between 8.5 and 10.5. The pH values for the purposes of the present invention are pH values which were measured at a temperature of 22° C.

Alkalizing agents usable according to the invention for establishing the preferred pH value may be selected from the group formed of ammonia, alkanolamines, basic amino acids, together with inorganic alkalizing agents such as alkali(ne earth) metal hydroxides, alkali(ne earth) metal metasilicates, alkali(ne earth) metal phosphates and alkali(ne earth) metal hydrogenphosphates. Preferred inorganic alkalizing agents are magnesium carbonate, sodium hydroxide, potassium hydroxide, sodium silicate and sodium metasilicate. Organic alkalizing agents usable according to the invention are preferably selected from monoethanolamine, 2-amino-2-methylpropanol and triethanolamine. The basic amino acids usable as alkalizing agents according to the invention are preferably selected from the group formed by arginine, lysine, ornithine and histidine, more preferably arginine.

In a further preferred embodiment, the action of the agent according to the invention may be enhanced by emulsifiers. Such emulsifiers are for example $C_{12}$-$C_{22}$ fatty acid mono- and diesters of addition products of 1 to 30 mol of ethylene oxide onto polyols having 3 to 6 carbon atoms, in particular onto glycerol, ethylene oxide and polyglycerol addition products onto methyl glucoside/fatty acid esters, fatty acid alkanolamides and fatty acid glucamides, $C_8$-$C_{22}$ alkyl mono- and oligoglycosides and the ethoxylated analogs thereof, with degrees of oligomerization of 1.1 to 5, in particular of 1.2 to 2.0, and glucose as the sugar component being preferred, mixtures of alkyl (oligo)glucosides and fatty alcohols, for example the commercially available product Montanov®68, addition products of 5 to 60 mol of ethylene oxide onto castor oil and hardened castor oil, phospholipids, above all glucose phospholipids which are for example obtained as lecithins, or phosphatidylcholines for example from egg yolk or plant seeds (for example soya beans), fatty acid esters of sugars and sugar alcohols, such as sorbitol, polyglycerols and polyglycerol derivatives such as for example polyglycerol poly-12-hydroxystearate (commercial product Dehymuls® PGPH), linear and branched fatty acids having 8 to 30 C atoms and the Na, K, ammonium, Ca, Mg and Zn salts thereof.

The agents according to the invention preferably include the emulsifiers in quantities of 0.1 to 25 wt. %, in particular of 0.5 to 15 wt. %.

Nonionogenic emulsifiers or surfactants with an HLB value of 10-15 may be more preferred according to the invention. Among the stated types of emulsifiers, those emulsifiers which include no ethylene oxide and/or propylene oxide in their molecule may be particularly preferred.

The oxidizing agent preparation and/or the alkalized second component may furthermore include further active substances, auxiliary substances and additives. A person skilled in the art will select these further substances in accordance with the desired properties of the agents. With regard to further optional components and the quantities of these components used, reference is explicitly made to the relevant handbooks known to a person skilled in the art, for example K h. Schräder, Grundlagen and Rezepturen der Kosmetika, 2nd edition, Hüthig Buch Verlag, Heidelberg, 1989. The additional active substances and auxiliary substances are preferably used in the agents according to the invention in quantities of in each case 0.0001 to 25 wt. %, in particular of 0.0005 to 15 wt. %.

The ready-to-use formulation for color modification of keratin fibers is produced shortly before use by mixing the oxidizing agent preparation with a second alkaline component. The oxidizing agent preparation according to the invention may in particular be mixed in excellent manner with the second component if a mixing dish is used for the mixing operation. If the two components are to be stirred together quickly, completely and homogeneously with a paintbrush or an applicette, it is essential for the viscosity of the oxidizing agent preparation to be within a specific range.

Oxidizing agent preparations which are suitable for the purposes of the present invention are distinguished in that, at 22° C., they have a viscosity of 70 to 900 mPa·s, preferably of 100 to 700 mPa·s, further preferably of 150 to 500 mPa·s and particularly preferably of 180 to 300 mPa·s. All the stated viscosity values here relate to values measured with a Brookfield RVT viscometer (rotational viscometer) at 22° C. with spindle 5 at 4 revolutions per minute (rpm).

A further particularly preferred embodiment of the present invention is characterized in that the oxidizing agent preparation has a viscosity of 70 to 900 mPa·s (22° C./Brookfield RVT viscometer/spindle 5/4 rpm).

In conventional commercial coloring or blonding products, the oxidizing agent preparation and the second component are usually offered for sale separately packaged in two bottles or containers. The contents of the two containers must be transferred as completely as possible into a mixing dish in order to produce the formulation for use. Adjusting the correct viscosity is likewise of crucial significance to ensuring maximally complete transfer from the container into the mixing dish. It is particularly important to provide the entire quantity of the oxidizing agent preparation which is present for the color modification process. The dispensing rate (stated in %) may be used as a quantitative measure of the possibility of discharging the oxidizing agent preparation from its container. The dispensing rate indicates the weight ratio of the oxidizing agent preparation dischargeable from the container to the total quantity present in the container. The higher the dispensing rate, the greater is the proportion of the oxidizing agent preparation which is available for the coloring or blonding process. Dispensing rates of below 90% are unacceptable from an economic and environmental standpoint.

The viscosity of the final mixture for use is decisively determined by the thickeners present in the oxidizing agent preparation. The viscosity of the mixture for use is here influenced by the nature of the thickener used, the input quantities thereof, their respective dependencies on temperature and pH and additional interactions which may occur when a plurality of thickeners are used with one another. While taking these influencing factors into account, the viscosity of the formulation for use must be adjusted such that the formulation for use is still of sufficiently low viscosity to wet the keratin fibers optimally and to ensure adequately rapid diffusion of oxidizing agent or dye precursors into the keratin fibers while at the same time not being of such low viscosity that the formulation drips off the keratin fibers.

It has been found that formulations for use having a viscosity within a range from 22000 to 30000 mPa·s optimally satisfy all requirements. Preferred oxidizing agent preparations are therefore furthermore characterized in that they include the components essential to the invention in quantities such that the viscosity of the formulation for use obtained after the mixing operation with a standardized alkaline component is within a range from 22000 to 30000 mPa·s, preferably from 23000 to 29000 mPa·s and more preferably from 24000 to 28000 mPa·s (22° C./Brookfield RVT viscometer/spindle 5/4 rpm).

The standardized alkaline component is taken in this connection to mean a conventional commercial cream which includes the following components which influence flow behavior: cetearyl alcohol (8.25 wt. %), Lorol technical ($C_{12}$-$C_{18}$ fatty alcohols) (2.75 wt. %), Ceteareth-20 (3.0 wt. %), Dehyquart A CA (INCI: Cetrimonium Chloride), 24-26% (3.0 wt. %), ammonia (25%, aqueous soln.) (6.9 wt. %).

The oxidizing agent preparations according to the invention are in particular suitable for use in a method for color modification of keratinic fibers, in particular human hair, which is characterized in that the oxidizing agent preparation of the first subject matter of the invention is mixed with a further, separately packaged agent including an alkalizing agent and optionally additionally oxidation dye precursors and/or substantive dyes, applied onto the keratin-containing fibers, left for 5 to 60 minutes on the fibers and then rinsed back out with water or washed out with a shampoo. The oxidizing agent formulation is preferably mixed with the second component in a mixing dish, wherein mixing proceeds by stirring with a paintbrush or with an applicette. The period of exposure for the ready-to-use coloring agent preferably amounts 5 to 45 min, in particular 10 to 40 min, more preferably 15 to 35 min. During the period of exposure of the fiber to the agent it may be advantageous to assist the lightening process by supplying heat. Exposure at room temperature is likewise according to the invention. In particular, the temperature during the period of exposure is between 20° C. and 40° C., in particular between 25° C. and 38° C. After the end of the period of exposure, the remaining coloring preparation is rinsed out of the hair with water or a cleaning agent. Conventional commercial shampoo may in particular be used here as the cleaning agent, wherein it is in particular possible to dispense with the cleaning agent and carry out the rinsing operation with water if the lightening or coloring agent has a carrier with a high surfactant content.

The present invention also provides a method for hair color modification which is characterized in that (I) an oxidizing agent preparation of the first subject matter of the invention is completely mixed together with (II) an agent containing an alkalizing agent and optionally additionally at least one oxidation dye precursor of the developer and/or coupler type and/or a substantive dye (III) in a mixing dish by stirring with a paintbrush or an applicette, (IV) the homogeneous mixture for use produced in this manner is applied with a paintbrush or an applicette onto the hair, (V) where it is left for a period of 5 to 60 minutes and (VI) then rinsed back out with water or a shampoo.

Prior to use, the oxidizing agent preparation and the component including the alkalizing agent are packaged separately from one another. The component including the alkalizing agent may additionally include one or more of the above-stated formulation components.

In a further embodiment, the ready-to-use formulation may be obtained by mixing 3 different components separately packaged from one another. The first component is the oxidizing agent preparation of the first subject matter of the invention and the second component is an alkalized formulation, both of which are mixed with a further, third component. Said third component may not only be a liquid component which is present in the form of a gel, an emulsion, a dispersion or a solution but, according to the invention, said third component may also be added as a solid in powder or tablet form to the other two components and mixed therewith by stirring.

Therefore, in a further preferred embodiment of the method according to the invention (I) an oxidizing agent preparation of the first subject matter of the invention is completely mixed together with (II) an agent including an alkalizing agent and optionally additionally at least one oxidation dye precursor of the developer and/or coupler type and/or a substantive dye (III) and a third, liquid or solid, component (IV) in a mixing dish by stirring with a paintbrush or an applicette, (V) the homogeneous mixture for use produced in this manner is applied with a paintbrush or an applicette onto the hair, (VI) where it is left for a period of 5 to 60 minutes and (VII) then rinsed back out with water or a shampoo.

This third component may include one or more of the above-stated formulation components. The third component preferably includes peroxo salts for enhancing the blonding or lightening action or structuring agents, hair-conditioning compounds, active substances which improve fiber structure, vitamins, provitamins and/or vitamin precursors.

It has been found over the course of the work leading to the present invention that even small quantities organic thickeners from the group of polysaccharides (c) are capable of adjusting the viscosity of oxidizing agent preparations including hydrogen peroxide (a) and organic lipophilic compound(s) (b) precisely, reliably and stably to a desired specification range.

The present invention also provides the use of organic thickeners from the group of polysaccharides (c) in a quantity range from 0.01 to 2.0 wt. % for adjusting the viscosity of oxidizing agent preparations which contain (a) 0.01 to 25.0 wt. % of hydrogen peroxide and (b) 0.01 to 15.0 wt. % of one or more organic lipophilic compound(s) from the group of plant and animal fats, oils and waxes, paraffin hydrocarbons, $C_{10}$-$C_{24}$ fatty alcohols, silicone oils and dialkyl ethers of formula (I), $$R1-O-R2 \quad (I)$$

in which

R1 and R2 mutually independently denote an unbranched or branched $C_8$-$C_{24}$ alkyl group.

The above statements regarding the agents according to the invention apply mutatis mutandis with regard to further preferred embodiments of the methods and use according to the invention.

Exemplary Embodiments

The following formulations were produced. The quantities given below are in weight percent unless stated otherwise.

1.1 Oxidizing Agent Preparations

| Formulation components (comparison) | Comparison 1 (wt. %) | Comparison 2 (wt. %) |
| --- | --- | --- |
| Sodium lauryl ether sulfate (INCI: Sodium Laureth Sulfate) | 2.00 | — |
| Cetyl alcohol | — | 3.5 |
| Ceteareth-20 | — | 0.5 |
| Ceteareth-30 | — | 1.5 |
| Sodium hydroxide, 45% technical | 0.73 | — |
| Potassium hydroxide, 50% | — | 0.15 |
| Dipicolinic acid | 0.1 | 0.1 |
| Disodium pyrophosphate | 0.03 | 0.03 |
| HEDP, 60% (INCI: Etidronic Acid) | 1.5 | 0.08 |
| Dow Corning DB 110 A (INCI: Dimethicone) | 0.07 | — |
| Aculyn 33A (INCI: Acrylates Copolymer), 27-29% | 10.0 | 10.0 |
| Hydrogen peroxide, 50% soln. | 22.4 | 12.0 |
| Water | Ad 100 | Ad 100 |

| Formulation component (according to the invention) | Invention 1 (wt. %) | Invention 2 (wt. %) | Invention 3 (wt. %) |
| --- | --- | --- | --- |
| Emulgade SE-PF | 4.5 | 4.5 | 4.5 |
| CETEARETH-12 | 2.0 | 2.0 | 2.0 |
| Myritol 331 | 3.0 | 3.0 | 3.0 |
| Cetiol CC (INCI: Dicaprylyl Carbonate) | 5.0 | 5.0 | 5.0 |
| Glycerol (96%) | 5.0 | 5.0 | 5.0 |
| Liquid paraffin | 10.0 | 10.0 | 10.0 |
| Dipicolinic acid | 0.1 | 0.1 | 0.1 |
| Disodium pyrophosphate | 0.1 | 0.1 | 0.1 |
| HEDP, 60% (INCI: Etidronic Acid) | 0.06 | 0.06 | 0.06 |
| Potassium hydroxide (50%) | 0.12 | 0.12 | 0.12 |
| Keltrol CG-SFT (INCI: Xanthan Gum) | 0.50 | 0.20 | 0.10 |
| Propylene glycol | 1.0 | 0.4 | 0.2 |
| Hydrogen peroxide, 50% soln. | 23.0 | 23.0 | 23.0 |
| Water (dist.) | Ad 100 | Ad 100 | Ad 100 |

Formulation components
Emulgade SE-PF: INCI: Glyceryl Stearate, Ceteareth-20, Ceteareth-12, Cetearyl Alcohol, Cetyl Palmitate
Myritol 331: Glycerides, mixed coco, decanoyl and octanoyl (INCI: Cocoglycerides)

1.2 Coloring Cream

The oxidizing agent preparations were in each case mixed in a 1:1 ratio with the following coloring cream in a mixing dish and intermixed using an applicette, giving rise to the mixtures for use. Coloring cream (CC)

| Formulation component | wt. % |
| --- | --- |
| Cetearyl alcohol | 8.25 |
| Lorol technical ($C_{12}$-$C_{18}$ fatty alcohols) | 2.75 |
| Ceteareth-20 | 3.0 |
| Dehyquart A CA (INCI: Cetrimonium Chloride), 24-26% | 3.0 |
| Sodium sulfite | 0.5 |
| Ammonium sulfate | 0.5 |

-continued

| Formulation component | wt. % |
|---|---|
| p-Tolylenediamine, sulfate | 0.7 |
| Resorcinol | 0.17 |
| 4-Chlororesorcinol | 0.30 |
| 4-Amino-3-methylphenol | 0.14 |
| p-Amino-o-cresol (5-amino-2-methylphenol) | 0.1 |
| HEDP, 60% (INCI: Etidronic Acid) | 0.2 |
| Ammonia (25%, aqueous soln.) | 6.9 |
| Ascorbic acid | 0.5 |
| Propylene glycol | 0.31 |
| Sodium silicate 42 | 0.5 |
| Gluadin W 40 (INCI: Hydrolyzed Wheat Protein) | 0.2 |
| Water (dist.) | Ad 100 |

1.3 Determination of Viscosities and Dispensing Rates

The viscosities of the oxidizing agent preparations and the mixtures for use were determined with a Brookfield RVT viscometer (rotational viscometer) at 22° C. (spindle 5/4 revolutions per minute) In addition, all the formulations were subjected to an objective expert evaluation with regard to their rheological properties. In addition, the environmental profile of the polymer used as thickener was evaluated.

Intrinsic Viscosity of the Oxidizing Agent Preparations

|  | Comparison 1 | Comparison 2 | Invention 1 | Invention 2 | Invention 3 |
|---|---|---|---|---|---|
| Viscosity (22° C., Brookfield, spindle 5/4 rpm) [mPa · s] | 30 | 5840 | 840 | 210 | 80 |
| Miscibility with coloring cream | immiscible | immiscible | readily miscible | readily miscible | readily miscible |
| Biopolymer as thickener | no | no | yes | yes | yes |

Dispensing rates were determined in order to assess transferability of the oxidizing agent preparation from the storage container into the mixing dish. The containers were to this end firstly filled with a defined quantity of the oxidizing agent preparation and were then left to stand for 24 hours. The containers were then emptied as completely as possible. The weight of the oxidizing agent preparation dischargeable from the container was determined by differential weighing. The dispensing rate is in each case obtained as the ratio of the weight of the discharged formulation to the total quantity present in the container.

Dispensing Rates

|  | Comparison 1 | Comparison 2 | Invention 1 | Invention 2 | Invention 3 |
|---|---|---|---|---|---|
| Dispensing rate | 98% acceptable | 63.5% not acceptable | 90% acceptable | 93% acceptable | 93% acceptable |

Viscosity of the Mixture for Use

|  | Comparison 1 + CC | Comparison 2 + CC | Invention 1 + CC | Invention 2 + CC | Invention 3 + CC |
|---|---|---|---|---|---|
| Viscosity (22° C., Brookfield, spindle 5/4 rpm) [mPa · s] | 30500 | 31500 | 24500 | 24200 | 25100 |

Comparison of all the results shows that it is only when the oxidizing agent preparations according to the invention are used that all requirements with regard to good miscibility and elevated dispensing rates can be satisfied.

The mixtures for use which were produced using the oxidizing agent preparations according to the invention have a viscosity range which is optimized with regard to convenience of use and coloring result.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for hair color modification, comprising:
   mixing an oxidizing agent preparation that includes:
   (a) 0.01 to 25.0 wt. % of hydrogen peroxide,
   (b) 0.01 to 15.0 wt. % of one or more organic lipophilic compound(s) selected from the group consisting of plant and animal fats, oils and waxes, paraffin hydrocarbons, $C_{10}$-$C_{24}$ fatty alcohols, silicone oils and dialkyl ethers of formula (I), $$R1\text{-}O\text{---}R2 \quad \quad (I)$$

in which
   R1 and R2 mutually independently denote an unbranched or branched $C_8$-$C_{24}$ alkyl group,
   (c) 0.01 to 2.00 wt. % of one or more organic thickeners selected from the group consisting of polysaccharides, and (d) at least one organic carbonate selected from the group consisting of the carbonates of formula (II) and formula (III),

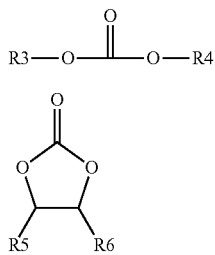

in which
R3, R4 mutually independently denote an unbranched $C_1$-$C_{30}$ alkyl group, a branched $C_3$-$C_{30}$ alkyl group or a mono- or polyunsaturated $C_2$-$C_{30}$ allyl group,
R5, R6 mutually independently denote hydrogen, an unbranched $C_1$-$C_{30}$ alkyl group, a branched $C_3$-$C_{30}$ alkyl group, a mono- or polyunsaturated $C_2$-$C_{30}$ alkyl group or a hydroxy-$C_1$-$C_6$-alkyl group,
with the proviso that the oxidizing agent preparation
  does not include a polymer which is obtained by polymerization or copolymerization of acrylic acid,
  does not include a polymer which is obtained by polymerization or copolymerization of methacrylic acid,
  does not include a polymer which is obtained by polymerization or copolymerization of acrylic acid esters, and
  does not include a polymer which is obtained by polymerization or copolymerization of methacrylic acid esters,
with an agent including an alkalizing agent and optionally additionally at least one oxidation dye precursor of the developer and/or coupler type and/or a substantive dye to form a homogenous mixture,
applying the homogeneous mixture onto the hair and leaving the applied mixture on the hair for a period of 5 to 60 minutes, and
rinsing the mixture out of the hair.

2. The method according to claim 1, wherein the oxidizing agent preparation includes as the organic lipophilic compound (b) 0.01 to 15.0 wt. % of at least one plant fat, at least one plant oil and/or paraffin hydrocarbons.

3. The method according to claim 1, wherein the oxidizing agent preparation includes as the polysaccharide (c) 0.01 to 2.0 wt. % of at least one anionic polysaccharide selected from the group consisting of carboxymethylcelluloses, alginic acids, xanthan gum and/or the physiologically acceptable salts thereof.

4. The method according to claim 1, wherein the oxidizing agent preparation includes as the anionic polysaccharide (c) 0.01 to 2.0 wt. % of xanthan gum.

5. The method according to claim 1, the oxidizing agent further comprising 0.1 to 10.0 wt. % of at least one organic solvent selected from the group consisting of 2-butoxyethanol, propylene glycol, propylene glycol monomethyl ether, diethylene glycol monomethyl ether, diethylene glycol monoethyl ether, ethylene glycol monobutyl ether, ethylene glycol monoethyl ether, ethanol, isopropanol, n-propanol, n-butanol, 1,2-propanediol, 1,3-propanediol, glycerol, 1-methoxy-2-propanol, 1-ethoxy-2-propanediol, 1,4-butanediol, 1,2-hexanediol, benzyl alcohol, phenoxyethanol, 2-phenylethyl alcohol, ethylene diglycol, methoxybutanol and n-butylene glycol.

6. The method according to claim 1, wherein the at least one organic carbonate is included at a concentration of 0.1 to 10.0 wt. % and is selected from the group consisting of dimethyl carbonate, diethyl carbonate, di-n-hexyl carbonate, di-n-octyl carbonate, di-n-decyl carbonate and di-n-dodecyl carbonate.

7. The method according to claim 1, the oxidizing agent further comprising 0.1 to 10 wt. % of at least one polyethoxylated fatty alcohol of formula (IV),

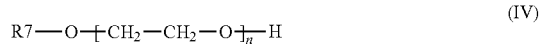

in which
R7 denotes an unbranched or branched, saturated or unsaturated $C_{10}$-$C_{24}$ alkyl group and
n denotes an integer from 2 to 80.

8. The method according to claim 1, wherein the oxidizing agent preparation has a viscosity of 70 to 900 mPa·s (22° C./Brookfield viscometer/spindle 5/4 rpm).

9. The method according to claim 1, wherein the oxidizing agent preparation comprises:
  (a) 0.01 to 25.0 wt. % of hydrogen peroxide,
  (b) 5.0 to 14.0 wt. % of paraffin hydrocarbons,
  (c) 0.1 to 2.0 wt. % of xanthan gum, and
  (d) 0.1 to 10.0 wt. % of the at least one organic carbonate.

10. The method according to claim 1, wherein the oxidizing agent preparation comprises:
  (a) 0.01 to 25.0 wt. % of hydrogen peroxide,
  (b) 8.0 to 13.5 wt. % of paraffin hydrocarbons,
  (c) 0.1 to 2.0 wt. % of xanthan gum, and
  (d) 0.1 to 10.0 wt. % of the at least one organic carbonate.

11. The method according to claim 1, wherein the oxidizing agent preparation comprises:
  (a) 0.01 to 25.0 wt. % of hydrogen peroxide,
  (b) 5.0 to 14.0 wt. % of paraffin hydrocarbons,
  (c) 0.1 to 1.0 wt. % of xanthan gum, and
  (d) 0.1 to 10.0 wt. % of the at least one organic carbonate.

12. The method according to claim 1, wherein the oxidizing agent preparation comprises:
  (a) 0.01 to 25.0 wt. % of hydrogen peroxide,
  (b) 8.0 to 13.5 wt. % of paraffin hydrocarbons,
  (c) 0.1 to 1.0 wt. % of xanthan gum, and
  (d) 0.1 to 10.0 wt. % of the at least one organic carbonate.

* * * * *